United States Patent [19]
Yokhin

[11] Patent Number: 6,041,095
[45] Date of Patent: Mar. 21, 2000

[54] X-RAY FLUORESCENCE ANALYZER

[75] Inventor: Boris Yokhin, Nazareth Illit, Israel

[73] Assignee: Jordan Valley Applied Radiation, Migdal Haemek, Israel

[21] Appl. No.: 09/028,588

[22] Filed: Feb. 24, 1998

[30] Foreign Application Priority Data

Mar. 12, 1997 [IL] Israel ......................................... 120429

[51] Int. Cl.⁷ ................................................ G01N 23/223
[52] U.S. Cl. ............................. 378/45; 378/44; 378/124
[58] Field of Search ................................. 378/45, 44, 46, 378/42, 49, 124

[56] References Cited

U.S. PATENT DOCUMENTS 3,919,548  11/1975  Porter .................................. 250/277
4,048,496   9/1977  Albert .................................. 250/272

*Primary Examiner*—David P. Porta
*Assistant Examiner*—Michael J. Schwartz
*Attorney, Agent, or Firm*—Christie, Parker & Hale, LLP

[57] ABSTRACT

Apparatus for X-ray excitation of a sample, including a substantially stationary X-ray source and X-ray optics, including at least one secondary target and a movable element. The movable element has at least a first position wherein X-rays emitted by the source excite the sample directly, and a second position wherein X-rays emitted by the source strike the at least one secondary target, causing the secondary target to emit X-rays that excite the sample, while the X-rays emitted by the source are substantially prevented from exciting the sample.

20 Claims, 5 Drawing Sheets

X-RAY FLUORESCENCE ANALYZER

FIELD OF THE INVENTION

The present invention relates generally to X-ray-based analytical instruments, and specifically to X-ray fluorescence analyzers.

BACKGROUND OF THE INVENTION

X-ray fluorescence (XRF) analyzers are well-known in the art, for determining the elemental composition of a sample. XRF analyzers generally include an X-ray source, which irradiates the sample, and an X-ray detector, for detecting the X-ray fluorescence emitted by the sample in response to the irradiation. Each element in the sample emits X-ray fluorescence in energy bands that are characteristic of the element. The detected X-ray fluorescence is analyzed to find the energies or, equivalently, the wavelengths of the detected photons, and the qualitative and/or quantitative composition of the sample is determined based on this analysis.

In order to produce strong fluorescence signals and detect a broad range of elements in a sample, XRF analyzers generally use an X-ray tube to irradiate the sample at a high X-ray flux. Such X-ray tubes generate a broad Brehmsstrahlung radiation spectrum, as is known in the art. The Brehmsstrahlung radiation excites the elements in the sample indiscriminately and may also scatter from the sample, creating a relatively high radiation background at the detector. In consequence, weak X-ray fluorescence signals emitted by trace elements of interest may be difficult or impossible to detect.

To overcome this problem, some XRF analyzers use secondary target excitation of the sample. The X-ray tube irradiates a secondary target of known, substantially pure elemental composition, typically a slug of a pure metal. The secondary target emits narrow-band, quasi-monochromatic radiation toward the sample at the known, characteristic X-ray emission lines of the secondary target. X-ray optics prevent the radiation from the X-ray tube from reaching the sample directly. The secondary target is typically chosen so that its characteristic emission lines coincide with one or more absorption bands of a trace element of interest in the sample. The Brehmsstrahlung background is thus substantially suppressed, and the strength of the X-ray fluorescence signal due to the trace element, relative to the background, is enhanced. Therefore, secondary target systems are generally capable of detecting trace elements at much lower concentration than ordinary, direct-excitation XRF analyzers.

Although secondary target excitation is advantageous in detection of specific trace elements, direct excitation of the sample by the X-ray tube is still faster and more convenient for analysis of one or multiple elements in moderate to high concentrations. Therefore, most laboratories will not purchase an XRF analyzer that offers only secondary target excitation, but rather require that the analyzer be capable of alternating between direct and secondary target excitation. Several such analyzers are commercially available.

FIG. 1, for example, is a schematic representation of an XRF detection system 20, similar to one that is used in the EDX 771 spectrometer, manufactured by Kevex of Valencia, Calif. System 20 comprises an X-ray tube 22 that can be shifted as indicated by an arrow 24 between a direct excitation position 26, in which tube 22 is shown by a solid line, and a secondary excitation position 28, in which the tube is shown by a dashed line. Radiation from tube 22 is directed via a selected one of a plurality of filters 30 and secondary targets 32, which are mounted on a filter and target wheel 34, toward a sample 36. X-ray fluorescence emitted by the sample is detected by a semiconductor detector 38, typically a Si(Li) (lithium-drifted silicon) detector, as is known in the art.

When tube 22 is in direct position 26, radiation from the tube passes directly through filter 30 and impinges on sample 36. Filter 30 comprises copper, for example, as is known in the art. In secondary position 28, however, tube 22 is aimed at secondary target 32, which comprises, for example, molybdenum. Radiation emitted by target 32 then impinges on sample 36. An X-ray baffle, not shown in the figure, prevents X-rays from tube 22 from striking sample 36 directly. Wheel 34 may be rotated to select among a plurality of different filters 30 and secondary targets 32.

Although system 20 allows both direct and secondary excitation of sample 36 using only a single X-ray tube 22, the movement of the tube introduces instability and, consequently, reduces the system's precision. Moreover, because of the mechanical constraints imposed by the need to move tube 22, the tube must be placed relatively far from filters 30, secondary targets 32 and sample 36. As a result, the detection efficiency of system 20, i.e., the strength of the signal received by detector 38 from a given sample relative to the power applied to drive tube 22, is comparatively low.

FIG. 2 is a schematic illustration of another XRF detection system 40, similar to one that is used in the EX-6500 XRF analyzer, manufactured by Jordan Valley Applied Radiation, of Migdal Haemek, Israel. System 40 is similar in operation to system 20, shown in FIG. 1, except that system 40 includes two X-ray tubes 42 and 44 instead of shiftable tube 22 in system 20. For direct excitation of sample 36, tube 42 is activated, whereas for secondary target excitation, tube 44 is used. System 40 thus overcomes the problem of instability described above with regard to system 20, but the need to use two X-ray tubes 42 and 44 increases the cost of the system. The mechanical constraints imposed on system 40 by the use of the two tubes 42 and 44 also lead to reduced detection efficiency.

SUMMARY OF THE INVENTION

It is an object of the present invention to provide improved apparatus for X-ray excitation of an analytical sample.

In accordance with some aspects of the present invention, the apparatus enables both direct and secondary target excitation of the sample, using a single, substantially stationary X-ray source.

It is a further object of some aspects of the present invention to provide an XRF detection system having improved detection efficiency and precision.

In preferred embodiments of the present invention, apparatus for X-ray excitation of a sample comprises an X-ray source, preferably a substantially stationary X-ray tube, and X-ray optics in proximity to the tube. The excitation apparatus is preferably used in an XRF detection system, wherein a detector, preferably substantially stationary, receives X-ray fluorescence emitted by the sample and generates signals responsive to the fluorescence. Signal analysis circuitry receives the fluorescence signals from the detector and analyzes the signals to determine the elemental composition of the sample, as is known in the art.

The X-ray optics comprise a movable element, including at least one secondary target and having at least a first and a second position. In the first position, X-rays from the X-ray tube pass through the optics to excite the sample directly. In the second position, X-rays from the tube strike the secondary target, which emits X-rays that excite the sample, while X-rays emitted by the tube are substantially prevented by the optics from reaching the sample. The X-ray tube is held stationary while the movable element is switched between the first and second positions, so that both direct and secondary-target excitation of the sample are achieved using a single tube in a fixed position.

In some preferred embodiments of the present invention, the movable element comprises a wheel, which is rotated around an axis thereof to switch between the first, direct excitation, position and the second, secondary-target excitation, position. More preferably, the wheel has a plurality of direct excitation positions and a plurality of secondary-target excitation positions. In each of the positions, X-rays from the tube enter a corresponding channel through the wheel. In the direct excitation positions, the corresponding channel is positioned generally along a beam axis from the X-ray tube to the sample. In the secondary-target excitation positions, the corresponding channel is positioned substantially eccentric to the beam axis, and a secondary target is placed in or adjacent to the channel, so that X-rays from the X-ray tube strike the secondary target, but substantially cannot reach the sample.

Preferably, in one or more of the direct excitation positions of the wheel, the corresponding channels contain filters, which filter the X-rays emitted by the X-ray tube before the rays reach the sample. Further preferably, in different ones of the plurality of direct excitation positions, the X-rays are filtered by different filters, for example, copper and rhodium; and in different ones of the plurality of secondary-target excitation positions, different secondary targets, for example, iron and molybdenum, are used to excite the sample.

In preferred embodiments of the present invention, the X-ray tube comprises a wide-angle emission tube, having a radiation cone angle of at least 30°. More preferably, the X-ray tube has a cone angle of at least 40°, and most preferably, the tube has a cone angle of approximately 46°, such as the EG60 tube, produced by Varian Corporation of Salt Lake City, Utah. By comparison, in XRF systems known in the art, the X-ray cone angle is limited to about 20°, either by internal geometry of the X-ray tube itself or by a collimator associated with the tube. The term "cone angle" as used in the present patent application and in the claims refers to the half-angle of the radiation cone emitted by the X-ray tube.

In preferred embodiments of the present invention, the movable element, preferably the wheel, is placed in close proximity to the wide-angle emission tube. As a result, both the on-axis channels, when direct excitation positions are selected, and the eccentric channels, when secondary-target positions are selected, receive substantial radiation without the necessity of moving the tube.

The close proximity of the tube to the secondary targets also increases the detection efficiency of the XRF system, since the flux of X-rays incident on the secondary targets is increased, thereby increasing the flux of X-rays emitted by the secondary target and incident on the sample. In the context of the present patent application and in the claims, the term "detection efficiency" is taken to mean the relative strength of detected X-ray fluorescence emitted by a given pure elemental sample for a certain voltage and current applied to the X-ray tube. Typically, detection systems in accordance with the principles of the present invention have detection efficiency at least 3–7 times greater than XRF detection systems known in the art.

There is therefore provided, in accordance with a preferred embodiment of the present invention, apparatus for X-ray excitation of a sample, including:

a substantially stationary X-ray source; and

X-ray optics, including at least one secondary target and a movable element having at least a first position wherein X-rays emitted by the source excite the sample directly, and a second position wherein X-rays emitted by the source strike the at least one secondary target, causing the secondary target to emit X-rays that excite the sample, while the X-rays emitted by the source are substantially prevented from exciting the sample.

Preferably, the X-ray source includes an X-ray tube having a radiation cone angle of at least 30°, more preferably at least 40°, and most preferably approximately 46°.

Preferably, the movable element includes first and second channels, which receive X-rays emitted by the source in the first and second positions of the element, respectively, and the at least one secondary target intercepts at least a portion of the rays received by the second channel. Preferably, the X-ray source has a beam axis, and in the first position, the first channel is generally aligned with the beam axis, whereas in the second position, the second channel is substantially eccentric to the beam axis.

In a preferred embodiment of the present invention, there is a filter associated with at least one of the first and second channels, which filters X-rays passing through the channel.

Preferably, the movable element includes a wheel, which is rotated about an axis thereof to pass between the first and second positions thereof. Further preferably, the channels pass through the wheel adjacent to the periphery thereof.

In a preferred embodiment of the present invention, the apparatus includes an X-ray detector, which is preferably substantially stationary, and which receives X-ray fluorescence emitted by the sample.

Preferably, the X-ray source includes a collimator, which allows X-rays to be emitted from the source over a substantially greater angle in a first emission plane, defined by the source, the sample and the detector, than in a second emission plane, perpendicular to the first emission plane.

There is further provided, in accordance with a preferred embodiment of the present invention, a method for X-ray excitation of a sample, including:

providing an X-ray source and X-ray optics, including a secondary target and a movable element, wherein in a first position of the movable element, X-rays emitted by the source pass through the optics to excite the sample directly; and shifting the movable element from the first position to a second position thereof while keeping the X-ray source substantially stationary, wherein in the second position of the element, X-rays emitted by the source strike the secondary target, causing the secondary target to emit X-rays that excite the sample, while the X-rays emitted by the source are substantially prevented from exciting the sample.

Preferably, the method includes filtering the X-rays that excite the sample.

Preferably, shifting the movable element to the second position thereof includes positioning a channel, which receives the X-rays emitted by the source, eccentrically relative to a beam axis of the source, preferably by rotating a wheel on which the secondary target is mounted.

In a preferred embodiment of the present invention, the sample is analyzed by receiving X-ray fluorescence emitted by the sample, responsive to the excitation, preferably by receiving fluorescence incident on a substantially stationary X-ray detector.

Preferably, the X-rays emitted by the source are collimated to form a beam having substantially greater angular extent in a first emission plane, defined by the source, the sample and the detector, than in a second emission plane, perpendicular to the first plane.

The present invention will be more fully understood from the following detailed description of the preferred embodiments thereof, taken together with the drawings in which:

DETAILED DESCRIPTION OF PREFERRED EMBODIMENTS

Figure 1:
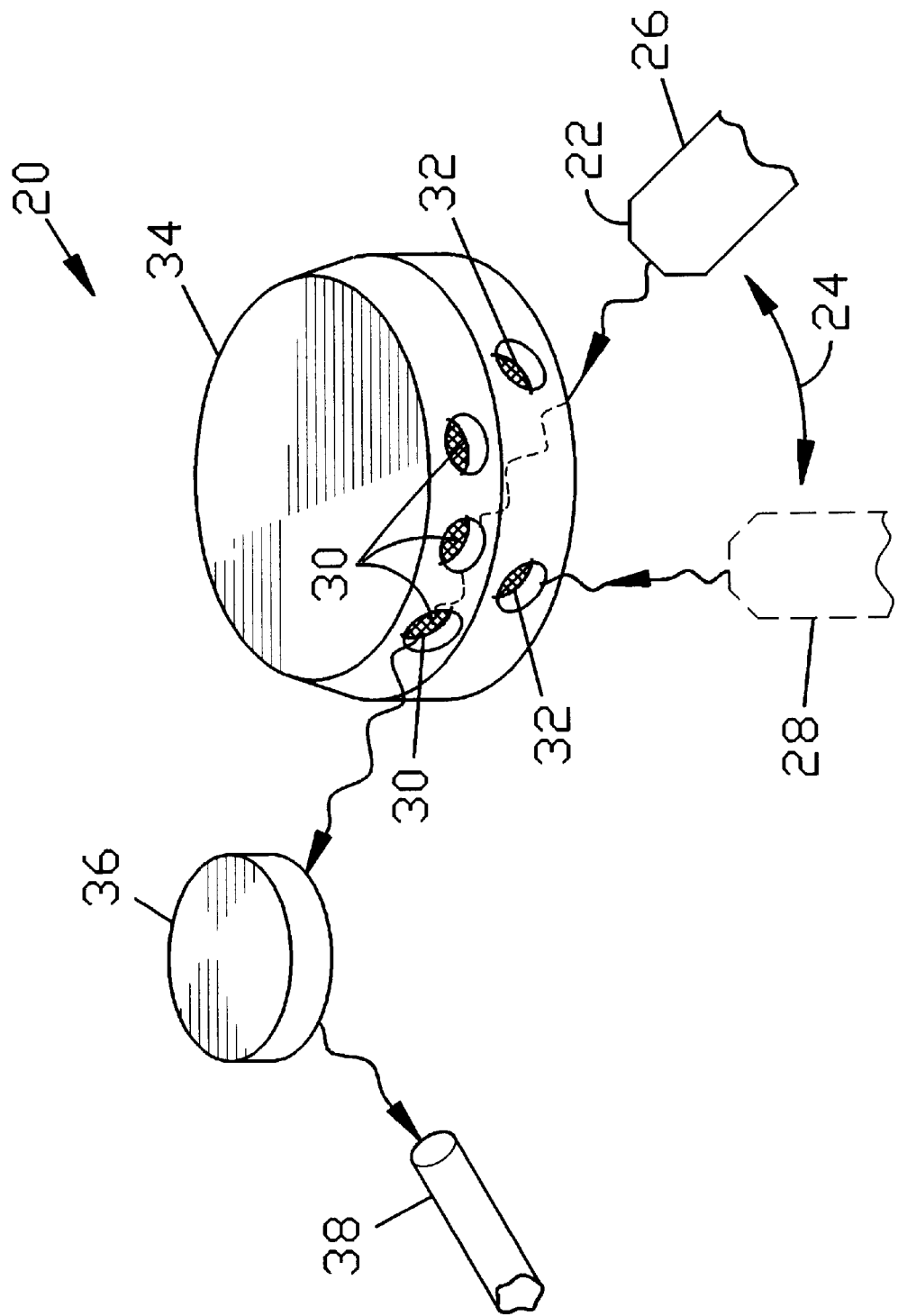
FIG. 1 is a schematic illustration showing an XRF detection system, known in the art.
Figure 3:
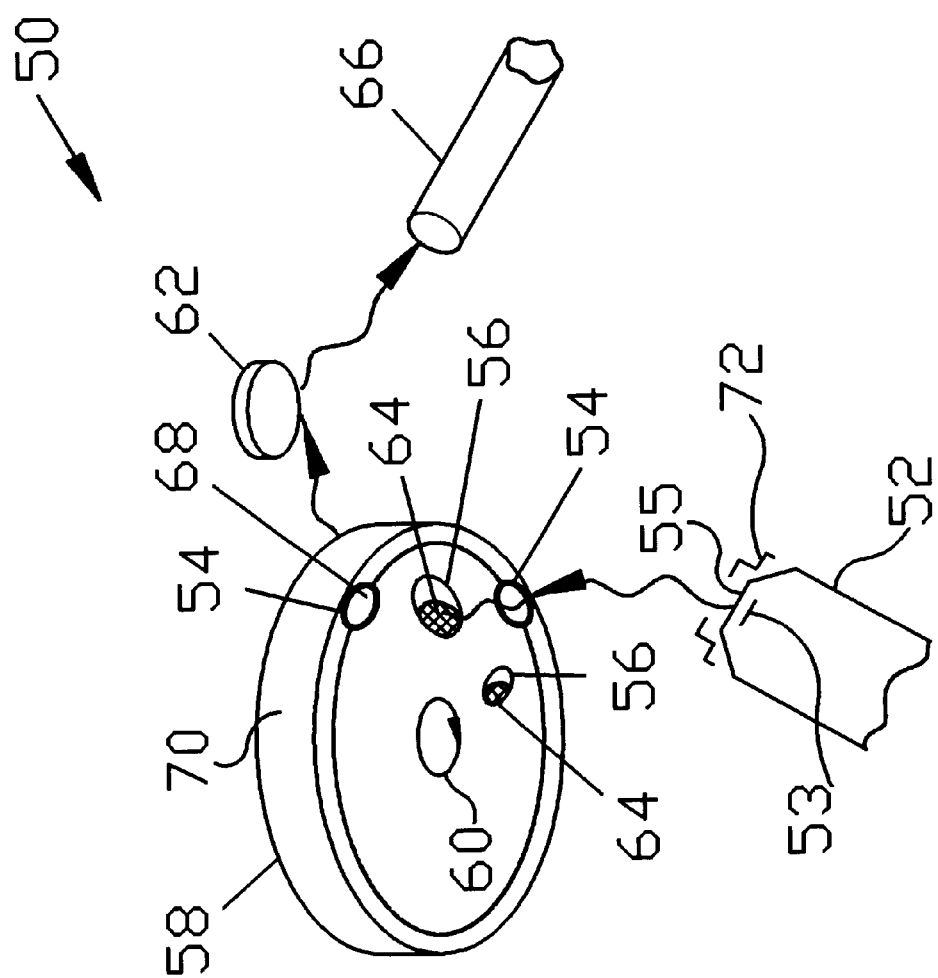
FIG. 3 is a schematic representation of an XRF detection system, in accordance with a preferred embodiment of the present invention.

Reference is now made to FIG. 3, which is a schematic representation of an XRF detection system 50, in accordance with a preferred embodiment of the present invention. System 50 comprises a substantially stationary, wide-angle X-ray tube 52, preferably an EG60 tube, manufactured by Varian Corporation, of Salt Lake City, Utah, which emits an X-ray beam having a cone angle of approximately 46°. Tube 52 comprises an anode 53 and a beryllium output window 55, and achieves this wide emission angle by virtue of the anode being close to the output window. The distance between anode 53 and window 55 is approximately 6 mm, by comparison with a typical distance of about 20 mm in a conventional X-ray tube, such as tube 22 (FIG. 1), which typically has a cone angle of about 20°. The wide beam angle of tube 52 is exploited by system 50 to achieve higher XRF detection efficiency than XRF systems known in the art, as described below.

X-rays emitted by tube 52 enter one of a plurality of direct excitation channels 54 and secondary-target excitation channels 56 in an optics wheel 58. Wheel 58 preferably comprises lead with an outer layer of silver-coated brass. The wheel rotates about a central axis thereof, as indicated by an arrow 60, so that any one of channels 54 and 56 may be selected and positioned in front of tube 52. When one of direct excitation channels 54 is positioned in front of the tube, X-rays emitted by the tube pass through the passage and strike a sample 62, exciting X-ray fluorescence thereof.

Alternatively, when one of secondary-target excitation channels ti is positioned in front of the tube, X-rays emitted by the tube strike a secondary target 64 positioned within the tube. The secondary target emits X-rays in response to the X-rays from tube 52 incident thereon. The X-rays emitted by secondary target 64 strike sample 62, exciting X-ray fluorescence thereof. At the same time, X-rays emitted by tube 52 are prevented from reaching the sample, as further described below with reference to FIG. 5.

In either case, whether sample 62 is irradiated via one of direct channels 54 or secondary-target channels 56, the X-ray fluorescence of sample 62 is detected by a detector 66, preferably a substantially stationary semiconductor detector, such as Si(Li), known in the art. The detected fluorescence is preferably analyzed, as is known in the art, to determine the elemental composition of the sample.

Figure 2:
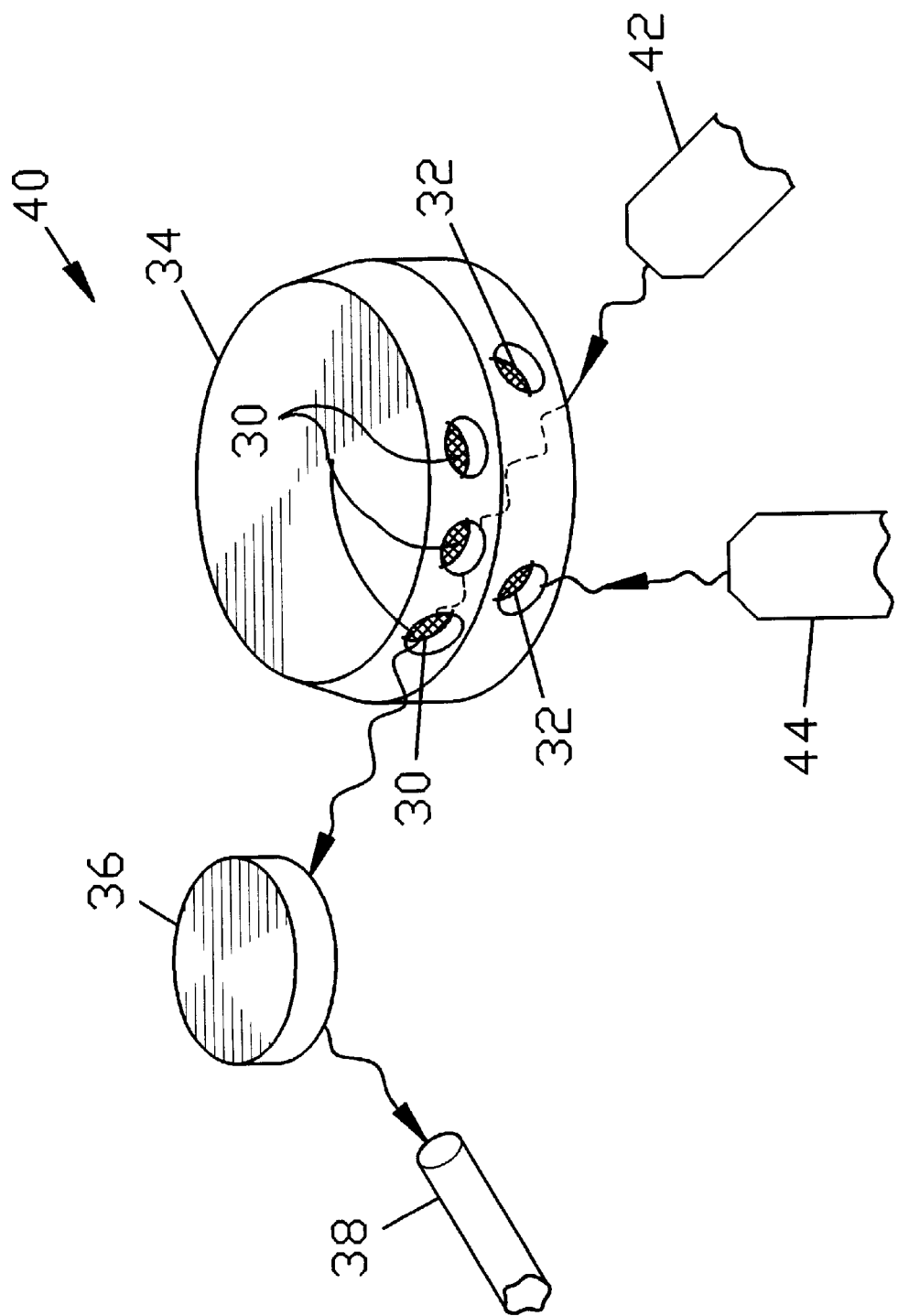
FIG. 2 is a schematic illustration of another XRF detection system, also known in the art.
Figure 4:
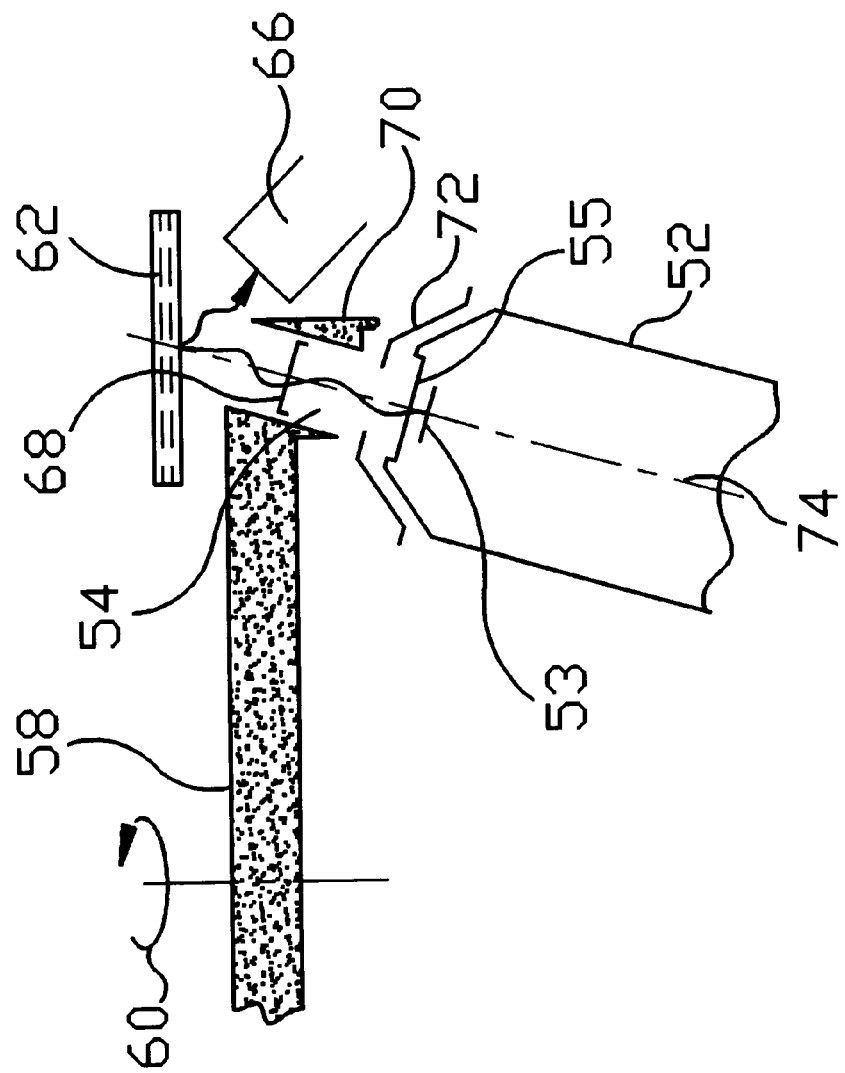
FIG. 4 is a schematic, sectional view of the system of FIG. 3 in a first position thereof, in which a sample is directly excited.
Figure 5:
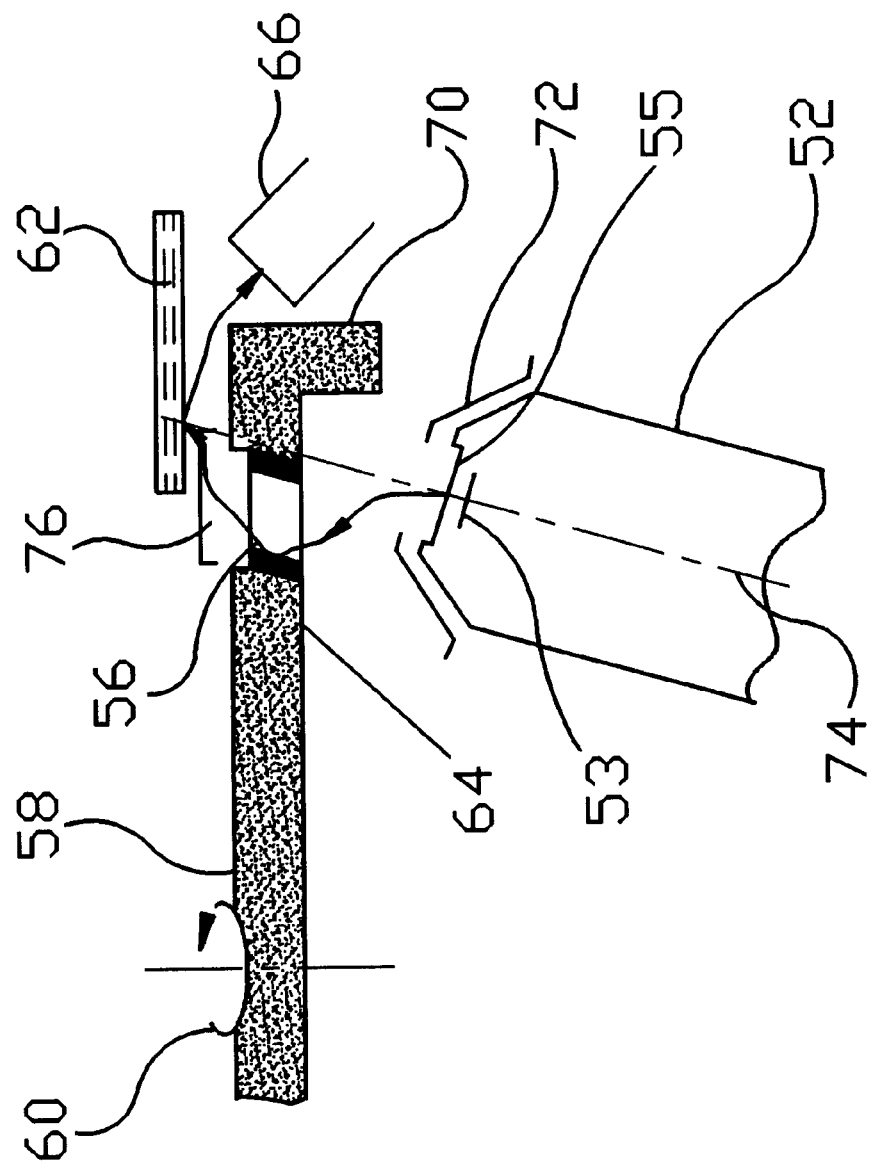
FIG. 5 is a schematic, sectional view of the system of FIG. 3 in a second position thereof, in which the sample undergoes secondary target excitation.

Preferably, channels 54 and 56 are located adjacent to periphery 70 of wheel 58, and wheel 58 is of a suitable size so that the wheel and detector 66 can be positioned close together, near sample 62. X-ray tube 52 is similarly positioned near wheel 58. Preferably, wheel 58 has a diameter of about 10 cm, and channels 54 and 56 have diameters of about 1 cm. Tube 52 and sample 62 are each positioned 1–2 cm from wheel 58, on opposite sides thereof, as shown in FIGS. 3–5. Such close mutual positioning of tube 52, wheel 58 and sample 62 enables the total useful flux of X-rays irradiating sample 62 to be increased. Similarly, because detector 66 is close to sample 62, it captures X-ray fluorescence emitted by the sample over a relatively large angle. Thus, on account of the high X-ray flux on the sample and the wide detection angle, system 50 has detection efficiency that is at least 3–7 times higher than that of XRF systems known in the art, such as systems 20 (FIG. 1) and 40 (FIG. 2), in direct excitation and at least 5–7 times higher than such systems in secondary-target excitation.

It will be appreciated that system 50 allows both direct and secondary-target excitation of sample 62 to be accomplished using only the single, stationary X-ray tube 52. This feature is made possible by the wide emission angle of tube 52 and by the design of wheel 58, which also contribute to the high detection efficiency of the system. Because system 50 uses only a single, stationary X-ray tube, it is generally more stable, and therefore more precise, than system 20 (FIG. 1), in which X-ray tube 22 moves between positions 26 and 28, and substantially lower in cost than system 40 (FIG. 2), with its two X-ray tubes 42 and 44. System 50 is also generally lower in cost than system 20, since system 50 has only a single moving part, wheel 58, whereas system 20 must also include a precision mechanism for shifting tube 22.

A collimator 72, preferably made of a lead-based alloy, as is known in the art, is preferably positioned between tube 52 and wheel 58, as shown in FIG. 3. Collimator 72 is preferably constructed so as to allow X-rays from tube 52 to pass therethrough within a relatively wide angle in the plane of the figure, i.e., a plane defined by the positions of tube 52, sample 62 and detector 66, while limiting the X-ray beam to a narrow angle outside the plane of the figure. Preferably, collimator 72 allows X-rays to pass therethrough within a cone angle of approximately 40° within the plane of the figure and within a beam angle of approximately 20° in a plane perpendicular to the plane of the figure. The collimator is useful in limiting the amount of stray radiation from tube 52 that is allowed to reach either sample 62 or detector 66.

FIG. 4 is a schematic, sectional representation of system 50, showing details of the direct excitation of sample 62 by x-ray tube 52. Wheel 58 is rotated so that one of direct excitation channels 54 is positioned in front of tube 52, whereby channel 54 is generally aligned with a central beam axis 74 of the tube. X-rays emitted by tube 52 pass through channel 54, traverse a filter 68, which filters the spectrum of X-rays passing therethrough, and strike sample 62. Although in FIG. 4, channel 54 and axis 74 are shown as being closely aligned, it will be understood that channel 54 may also be somewhat off axis 74, by about 10°, for example, as long as the X-rays from tube 52 can reach sample 62 directly through the channel. X-ray fluorescence emitted by the sample is detected by detector 66, as described above.

Preferably, each of direct channels 54 contains a different filter 68. Filters 68 include, for example, Ti, Fe, Cu, Mo, Rh and Sn, as are known in the art. Preferably, however, one of channels 54 contains no filter, so that the sample may be irradiated using the entire spectrum emitted by the tube.

FIG. 5 is a schematic, sectional representation of system 50, showing details of secondary-target excitation of sample 62. X-rays from tube 52 enter channel 56, which is positioned eccentrically with respect to beam axis 74. The X-rays emitted by the tube strike secondary target 64 in channel 56, but are substantially prevented by the shape and eccentricity of the channel from reaching sample 62. X-rays emitted by secondary target 64 strike sample 62, whose resulting X-ray fluorescence is then detected by detector 64.

Preferably, each of secondary-target channels 56 contains a different secondary target 64, preferably including some or all of Mg, Si, Ti, Fe, Cu, Ge, Mo and Gd. As is known in the art, each secondary target 64 emits X-rays in a different, characteristic, narrow band of energies, useful in exciting different elements in sample 62. Further preferably, a filter 76, similar to filters 68, is placed across channel 56, so as to further narrow the band of radiation reaching sample 62.

Although the above preferred embodiment is described with reference to rotatable optics wheel 58, which is used to switch between direct and secondary-target excitation of sample 62, it will be appreciated that in other preferred embodiments of the present invention, other types of X-ray optics may similarly be used for this purpose. For example, a linear slide containing direct and secondary target channels may be used in place of wheel 58.

It will be appreciated that the preferred embodiments described above are cited by way of example, and the full scope of the invention is limited only by the claims.

I claim:

1. Apparatus for X-ray excitation of a sample, comprising:
   a substantially stationary X-ray source; and
   X-ray optics, comprising at least one secondary target and a movable element having at least a first position wherein X-rays emitted by the source excite the sample directly, and a second position wherein X-rays emitted by the source strike the at least one secondary target, causing the secondary target to emit X-rays that excite the sample, while the X-rays emitted by the source are substantially prevented from exciting the sample.

2. Apparatus for X-ray excitation of a sample, comprising:
   a substantially stationary X-ray source, wherein the X-ray source comprises an X-ray tube having a radiation cone angle of at least 30°; and
   X-ray optics, comprising at least one secondary target and a movable element having at least a first position wherein X-rays emitted by the source excite the sample directly, and a second position wherein X-rays emitted by the source strike the at least one secondary target, causing the secondary target to emit X-rays that excite the sample, while the X-rays emitted by the source are substantially prevented from exciting the sample.

3. Apparatus according to claim 2, wherein the X-ray tube has a cone angle of at least 40°.

4. Apparatus according to claim 3, wherein the X-ray tube has a cone angle of approximately 46°.

5. Apparatus according to claim 1, wherein the movable element comprises first and second channels, which receive X-rays emitted by the source in the first and second positions of the element, respectively, and wherein the at least one secondary target intercepts at least a portion of the rays received by the second channel.

6. Apparatus according to claim 5, wherein the X-ray source has a beam axis, and wherein in the first position, the first channel is generally aligned with the beam axis.

7. Apparatus according to claim 6, wherein in the second position, the second channel is substantially eccentric to the beam axis.

8. Apparatus according to claim 5, and comprising a filter associated with at least one of the first and second channels, which filters X-rays passing through the channel.

9. Apparatus according to claim 5, wherein the movable element comprises a wheel, and wherein the wheel is rotated about an axis thereof to pass between the first and second positions thereof.

10. Apparatus according to claim 9, wherein the channels pass through the wheel adjacent to the periphery thereof.

11. Apparatus according to claim 1, and comprising an X-ray detector, which receives X-ray fluorescence emitted by the sample.

12. Apparatus according to claim 11, wherein the detector is substantially stationary.

13. Apparatus according to claim 12, wherein the X-ray source comprises a collimator, which allows X-rays to be emitted from the source over a substantially greater angle in a first emission plane, defined by the source, the sample and the detector, than in a second emission plane, perpendicular to the first emission plane.

14. A method for X-ray excitation of a sample, comprising:
   providing an X-ray source and X-ray optics, including a secondary target and a movable element, wherein in a first position of the movable element, X-rays emitted by the source pass through the optics to excite the sample directly; and
   shifting the movable element from the first position to a second position thereof while keeping the X-ray source substantially stationary, wherein in the second position of the element, X-rays emitted by the source strike the secondary target, causing the secondary target to emit X-rays that excite the sample, while the X-rays emitted by the source are substantially prevented from exciting the sample.

15. A method according to claim 14, and comprising filtering the X-rays that excite the sample.

16. A method according to claim 14, wherein shifting the movable element to the second position thereof comprises positioning a channel, which receives the X-rays emitted by the source, eccentrically relative to a beam axis of the source.

17. A method according to claim 14, wherein shifting the movable element comprises rotating a wheel on which the secondary target is mounted.

18. A method according to claim 14, and comprising analyzing the sample by receiving X-ray fluorescence emitted by the sample, responsive to the excitation.

19. A method according to claim 18, wherein receiving the X-ray fluorescence comprises receiving fluorescence incident on a substantially stationary X-ray detector.

20. A method according to claim 19, and comprising collimating the X-rays emitted by the source to form a beam having substantially greater angular extent in a first emission plane, defined by the source, the sample and the detector, than in a second emission plane, perpendicular to the first plane.

* * * * *